US005695967A

United States Patent [19]
Van Bokkelen et al.

[11] Patent Number: 5,695,967
[45] Date of Patent: Dec. 9, 1997

[54] METHOD FOR STABLY CLONING LARGE REPEATING UNITS OF DNA

[75] Inventors: Gil B. Van Bokkelen, Los Altos, Calif.; John J. Harrington, Cleveland; Huntington F. Willard, Shaker Heights, both of Ohio

[73] Assignee: Case Western Reserve University, Cleveland, Ohio

[21] Appl. No.: 487,989

[22] Filed: Jun. 7, 1995

[51] Int. Cl.$^6$ .................................................. C12P 19/34
[52] U.S. Cl. ................ 435/91.1; 435/252.3; 435/252.33; 435/320.1; 435/172.3
[58] Field of Search ............................ 435/240.4, 240.1, 435/320.1, 172.3, 69.2, 69.4, 91.2, 91.1, 252.3, 252.33; 536/23.1, 23.5

[56] References Cited

U.S. PATENT DOCUMENTS

| | | | |
|---|---|---|---|
| 5,049,504 | 9/1991 | Maugh et al. | 435/252.33 |
| 5,149,657 | 9/1992 | Maugh et al. | 435/320.1 |
| 5,202,236 | 4/1993 | Maugh et al. | 435/69.1 |
| 5,202,256 | 4/1993 | Maugh et al. | 435/252.3 |
| 5,242,808 | 9/1993 | Maugh et al. | 435/69.1 |
| 5,288,625 | 2/1994 | Hadlaczky | 435/172.2 |

FOREIGN PATENT DOCUMENTS

WO 91/07496  5/1991  WIPO .................................. 435/320.1

OTHER PUBLICATIONS

Pan, A. et al. 1993. Protein Engineering vol. 6 (7): 755–762.
Sambrook, J. et al. 1989. Molecular Cloning, A Laboratory Manual. Second Ed. Cold Spring Harbor Press.
Waye, J.S. et al. 1986. Molecular and Cellular Biology vol. 6: 3156–3165.
Shizuyo, H. et. al. 1992 Proc. Natl. Acad. Sci USA vol. 89: 8794–8797.
Brown, K.E. et al., "Dissecting the centromere of the human Y chromosome with cloned telomeric DNA," *Hum. Mol. Genet.* 3(8):1227–1237 (Aug. 1994).
Brutlag, D. et al., "Synthesis of Hybrid Bacterial Plasmids Containing Highly Repeated Satellite DNA," *Cell* 10(3):509–519 (1977).
Haaf, T. et al., "Integration of Hyman α–Satellite DNA into Simian Chromosomes: Centromere Protein Binding and Disruption of Normal Chromosome Segregation," *Cell* 70(4):681–696 (1992).
Hosoda, F. et al., "An F factor based cloning system for large DNA fragments," *Nucleic Acids Res.* 18(13):3863–3869 (1990).
Kellogg, D.R. et al., "The Centrosome and Cellular Organization," *Annu. Rev. Biochem.* 63:639–674 (Jul. 1994).
Larin, Z. et al., "De novo formation of several features of a centromere following introduction of a Y alphoid YAC into mammalian cells," *Hum. Mol. Genet.* 3(5):689–695 (May 1994).
Leonhardt, H. and Alonso, J.C., "Parameters affecting plasmid stability in *Bacillus subtilis*," *Gene* 103:107–111 (1991).

Neil, D.L. et al., "Structural instability of human tandemly repeated DNA sequences cloned in yeast artificial chromosome vectors," *Nucleic Acids Res.* 18(6):1421–1428 (1990).
Oakey, R. and Tyler–Smith, C., "Y Chromosome DNA Haplotyping Suggests That Most European and Asian Men Are Descended from One of Two Males," *Genomics* 7:325–330 (1990).
O'Connor, M. et al., "Construction of Large DNA Segments in *Escherichia coli*," *Science* 244:1307–1312 (1989).
Schalkwyk, L.C. et al., "Techniques in mammalian genome mapping," *Curr. Opin. Biotech.* 6:37–43 (1995).
Shizuya, H. et al., "Cloning and stable maintenance of 300–kilobase–pair fragments of human DNA in *Escherichia coli* using an F–factor–based vector," *Proc. Natl. Acad. Sci. USA* 89:8794–8797 (Sep. 1992).
Sinden, R.R. et al., "On the Deletion of Inverted Repeated DNA in *Escherichia coli*: Effects of Length, Thermal Stability, and Cruciform Formation in Vivo," *Genetics* 129:991–1005 (1991).
Tyler–Smith, C. and Willard, H.F., "Mammalian chromosome structure," *Curr. Opin. Genet. Develop.* 3:390–397 (1993).
Waye, J.S. and Willard, H.F., "Nucleotide sequence heterogeneity of alpha satellite repetitive DNA: a survey of alphoid sequences from different human chromosomes," *Nucleic Acids Res.* 15(18):7549–7569 (1987).
Waye, J.S. and Willard, H.F., "Structure, Organization, and Sequence of Alpha Satellite DNA from Human Chromosome 17: Evidence for Evolution by Unequal Crossing–Over and an Ancestral Pentamer Repeat Shared with the Human X Chromosome," *Molec. Cell. Biol.* 6(9):3156–3165 (1986).
Wevrick, R. and Willard, H.F., "Long–range organization of tandem arrays of α satellite DNA at the centromeres of human chromosomes: High–frequency array–length polymorphism and meiotic stability," *Proc. Natl. Acad. Sci. USA* 86(23)9394–9398 (1989).
Willard, H.F., "Centromeres of mammalian chromosomes," *TIG* 6(12):410–415 (1990).
Willard, H.F. and Davies, K.E., "Mammalian genetics," *Curr. Opin. Genet. Develop.* 3:387–389 (1993).
Willard, H.F. et al., "Human Centromere Structure: Organization and Potential Role of Alpha Satellite DNA," In: *Mechanisms of Chromosome Distribution and Aneuploidy*, Resnick et al. eds., pp. 9–18 (1989).
Hartley, J.L. and Gregori, T.J., "Cloning multiple copies of a DNA segment," *Gene* 13:347–353 (1981).
Hofer, B., "Construction and stability of a sixfold repeated artificial gene," *Eur. J. Biochem.* 167:307–313 (1987).

(List continued on next page.)

*Primary Examiner*—James Ketter
*Assistant Examiner*—Iran Yucel
*Attorney, Agent, or Firm*—Sterne, Kessler, Goldstein & Fox P.L.L.C.

[57] ABSTRACT

A direction method of stably cloning large repeating units of DNA is described. The method is especially useful for the stable cloning of alpha satellite DNA.

20 Claims, 2 Drawing Sheets

OTHER PUBLICATIONS

Hwang, E.S. and Scocca, J.J., "A Method of Cloning Multiple Direct Repeats of a DNA Segment." *BioTechniques* 14(5):766–767 (1993).

Rosenfeld, P.J. and Kelly, T.J., "Purification of Nuclear Factor I by DNA Recognition Site Affinity Chromotography," *J. Biol. Chem.* 261(3):1398–1408 (1986).

Taylor, W.H. and Hagerman, P.J., "A general method for cloning DNA fragments in multiple copies," *Gene* 53:139–144 (1987).

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

GGGCGGGAGA TCTCAGAAAA TTCTTTGGGA TGATTGAGTT G     41

( 2 ) INFORMATION FOR SEQ ID NO:2:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:2:

GGGCGGGATC CCTTCTGTCT TCTTTTATA GGAAGTTATT T     41

METHOD FOR STABLY CLONING LARGE REPEATING UNITS OF DNA

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

FIELD OF THE INVENTION

This invention relates to the field of gene therapy and gene therapy vector technology. It also relates to the development and practical use of synthetic human chromosomes, or synthetic chromosomes in related primates or other mammals.

BACKGROUND OF THE INVENTION

The ability to clone large, highly repetitive DNA is an important step toward the development and construction of a human artificial microchromosome, and gene therapy vehicles. In addition, stable cloning of repetitive DNA in microorganisms will be important for generating high resolution physical maps of mammalian chromosomes.

A variety of cloning systems have been developed to facilitate the cloning and propagation of foreign DNA in micro-organisms. Plasmids, bacteriophage, and yeast artificial chromosomes (YACs) have been used successfully to clone many mammalian DNA sequences. However, some types of repetitive DNA appear to be unstable in these vectors (Schalkwyk et al., *Curr. Opin. Biotechnol.* 6(1): 37–43 (1995); Brutlag, D. et al., *Cell* 10: 509–519 (1977)). This results in gaps in physical genomic maps and precludes the use of these vectors as a means of propagating highly repetitive mammalian centromeric DNA.

Bacterial Artificial Chromosomes (BACs) have been constructed to allow the cloning of large DNA fragments in *E. coli* (O'Conner et al., *Science* 244 (4910): 1307–12 (1989); Shizuya et al., *Proc. Natl. Acad. Sci. USA* 89 (18): 8794–7 (1992); Hosoda et al., *Nucleic Acids Res.* 18(13): 3863–9 (1990)). While this system appears to be capable of stably propagating mammalian DNA up to at least 300 kb, relatively few independent mammalian DNA fragments have been analyzed (Shizuya et al., *Proc. Natl. Acad. Sci. USA* 89 (18): 8794–7 (1992)). In addition, the few fragments that have been tested for stability in the BAC vector, have not been extensively characterized with respect to the types of sequences present in each fragment. Thus, it is unknown whether these fragments contain repetitive DNA elements. In particular, it is clear, based on the restriction site and Southern analysis, that these fragments do not contain alpha satellite DNA.

Many mammalian DNA sequences appear stable in Yeast Artificial Chromosome (YAC) vectors, and yet certain repetitive elements of similar length are not (Neil et al., *Nucleic Acids Res.* 18(6): 1421–8 (1990)). Knowledge of DNA properties derived from the YAC system thus suggests that large arrays of repeating units are inherently unstable, even under conditions where similar sized DNA composed of non-repeating DNA is stable. Thus, the stability of large (greater than 100 kb) arrays of repeating units such as is found in alpha satellite DNA in the BAC vector cannot be predictable with any reasonable certainty. In addition, even if some alpha satellite arrays are stable in the BAC vector, a priori, it is not clear whether arrays of sufficient size and sequence composition to facilitate centromere function will be capable of being stably propagated in this vector.

SUMMARY OF THE INVENTION

It is an object of this invention to describe a method for construction of uniform or hybrid synthetic arrays of repeating DNA, and especially, alpha satellite DNA. It is a further object of the invention to describe a method for the cloning, propagation, and stable recombinant production of repeating DNA, and especially, naturally occurring or synthetic alpha satellite arrays.

Accordingly, the invention is directed to a method for stably cloning large repeating DNA sequences, vectors containing the above arrays, and hosts transformed with such vectors.

DETAILED DESCRIPTION OF THE PREFERRED EMBODIMENTS

By "stably transformed" is meant that the cloned DNA array containing the repeating units is capable of being propagated in the desired host cell for at least 50 generations of growth with a recombination frequency of less than 0.6% per generation (for 174 kb arrays) and a recombination frequency of less than 0.2% (for 130 kb arrays). Arrays smaller than 130 kb exhibit little or no recombination when cloned by the method of the invention.

By "higher order repeat" is meant a repeating unit that is itself composed of smaller (monomeric) repeating units. The basic organizational unit of alpha satellite arrays is the approximately 171 bp alphoid monomer. Monomers are organized into chromosome-specific higher order repeating units, which are also tandemly repetitive. The number of constituent monomers in a given higher order repeat varies, from as little as two (for example, in human chromosome 1) to greater than 30 (human Y chromosome). Constituent monomers exhibit varying degrees of homology to one another, from approximately 60% to virtual sequence identity. However, higher order repeats retain a high degree of homology throughout most of a given alphoid array.

The method of the invention provides a method of stably cloning highly repetitive regions of DNA, in microorganisms. Arrays of defined length, composition, orientation and phasing are possible. By proper phasing is meant that the precise length and orientation of any given higher order repeat in the array is not altered from that in the naturally-occurring sequence by the construction of the array, and also that there is no non-repeating DNA at the junction of the repeating units. For alphoid sequences, for example, the length and orientation of the higher order repeating unit is exactly the same as the naturally-occurring higher order repeat, and there is no non-alphoid sequences present at the junction of the higher order repeats, except for the bases modified to create the restriction sites.

Accordingly, a method for cloning repeating tandem arrays of DNA is provided, wherein a first DNA unit is prepared such that the opposing ends of the DNA unit contain complementary, but non-isoschizomeric restriction sites. This DNA is ligated into a vector, and the vector is lineaxized at one of the restriction sites. A second DNA unit, prepared as in step (a), is then ligated in tandem with said first unit, so as to form a directional, repeating array. This array is transformed into a host cell, and especially a bacterial host cell, and stable clones containing said array are selected. Starting with the vector linearization, these steps are repeated until a desired array size is reached.

Figure 1:
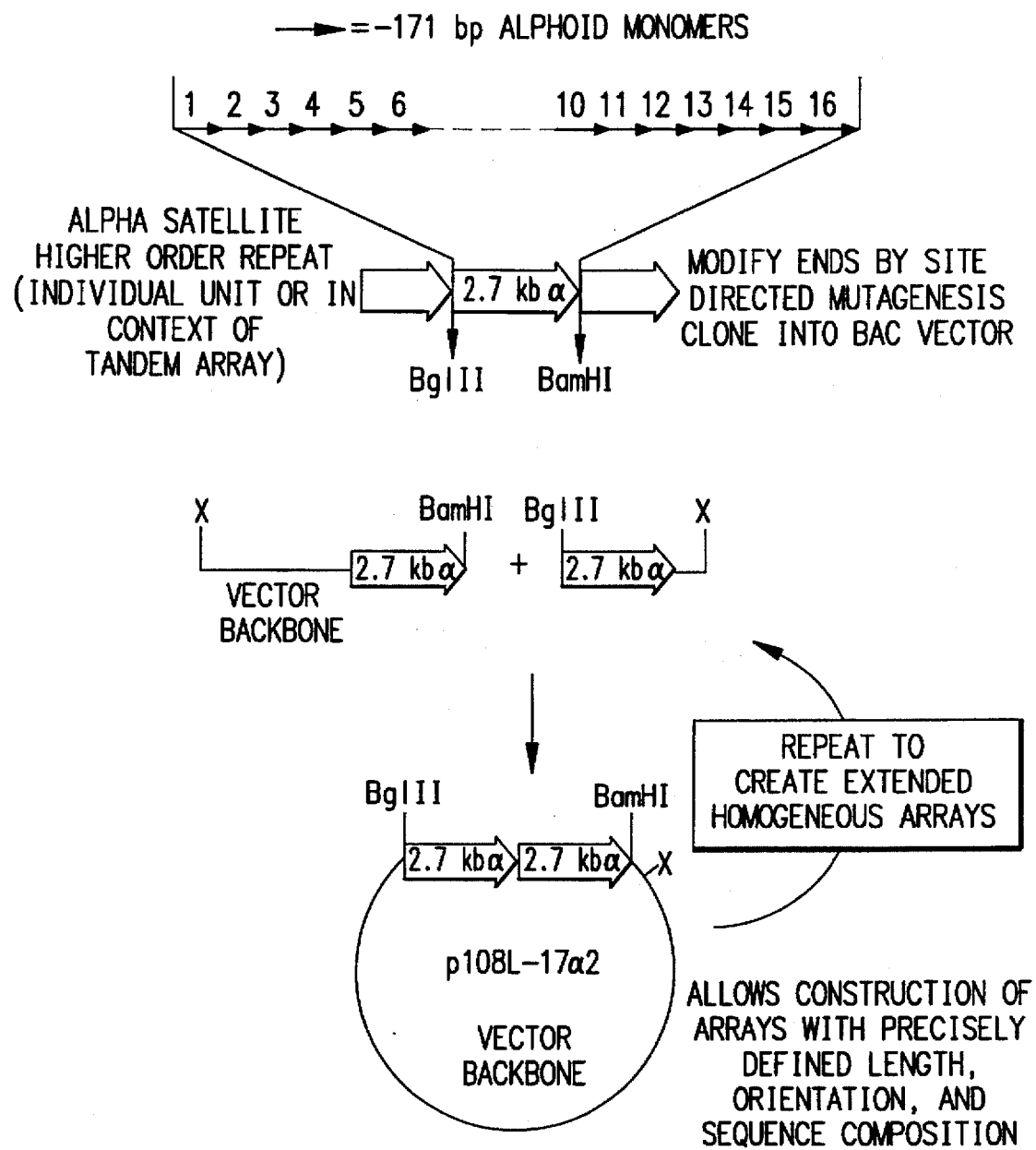
FIG. 1 is a schematic diagram of the method of the invention. The numbers "1–16" represent 1–16 copies of monomeric units (of approximately 171 bp) of alpha satellite DNA, tandemly aligned in a linear array. "X" represents a desired restriction enzyme site in the backbone of the vector carrying the array during its expansion to a desired size.

The directional cloning scheme of the invention is illustrated in FIG. 1, wherein the cloning of alpha satellite DNA higher order repeats is illustrated. As shown in the figure, the method of the invention utilizes a "build-up" approach, wherein shorter units, preferably higher order repeats, are added together to create the longer tandem array of repeating units. The units are added to each other in a manner that results in a defined orientation, which is established by two different restriction sites—one at each end of each repeating unit. Preferably, the repeating unit, and especially the higher order repeating unit, that is the basis of the tandem array contains complementary, but non-isoschizomeric restriction sites at opposing ends. Such ends may be designed into the unit using methods such as polymerase chain reaction (PCR). In the method of the invention, by complementary ends, it is intended to include both complementary overhanging ends and blunt ends.

In a preferred embodiment, the DNA array is alphoid DNA. As shown in Example 1, polymerase chain reaction (PCR) can be used to amplify a single 2.7 kb DNA alphold unit (actual length 2.712 kb) such that complementary restriction sites (BamH I and Bgl II) are created at opposing ends of the higher order register of alpha satellite repeat from human chromosome 17. The ends of the higher order repeats can be modified using polymerase chain reaction mediated site directed mutagenesis so that complementary restriction sites are created at opposite ends of each repeat. The modified higher order repeats are then cloned into the mini-F cloning vector pBAC108L (Shizuya, H. et al., *Proc. Natl. Acad, Sci. USA* 89: 8794–8797 (1992), incorporated herein by reference). These complementary restriction sites are used in conjunction with non-complementary flanking restriction sites to directly clone synthetic arrays of alpha satellite DNA derived from a single modified higher order repeat (FIG. 1). Synthetic arrays can be created from any higher order alphold repeat, including such alphoid DNA derived from chromosome 17, the Y chromosome, or other chromosome. In addition, hybrid arrays consisting of higher order repeats from both chromosomes can be prepared. In a preferred embodiment, the DNA is human DNA.

Arrays up to 200–215 kb are stable in the vector and hosts of the invention. In one embodiment, an array of 87 kb–215 kb in length is constructed. In a preferred embodiment, an array of at least 100 kb in length is constructed. In a highly preferred embodiment, an array of at least 140 kb, and especially at least 174 kb in length is constructed; arrays of 174 kb exceed the minimum known observed length of a functional alpha satellite array.

Examples of useful complementary, but non-isoschizomeric restriction enzymes that are useful in creating such sites include: Sal I and Xho I; Mun I and EcoR I; Afl III and Nco I/Sty I (isoschizomers: either one can be the partner for the non-isoschizomer partner); Nhe I and Xba I and Sty I/Avr II (isoschizomers) and Spe I (any combination); Cla I and BstB I and Acc I (any combination); Mlu I/Afl III (isoschizomers) and BssH II and Asc I; and Not I and Eag I. Bcl I is a complementary/non-isoschizomer of both BamH I and Bgl II.

The amplified DNA is then digested using, for example, (1) BamH I+Sfi I, or (2) Bgl II+Sfi I. Following separation of the bands in the digested DNA using physical methods capable of separating such DNA, such as, for example, gel electrophoresis, the DNA band from one digest is excised and ligated to the excised DNA band from the other digest. In the above example, since Bgl II and BamH I generate compatible overhangs, and Sfi I generates an asymmetric overhang that can only religate in a particular orientation, DNA flanked by these sites ligates to the vector DNA to create a tandem dimer arrayed in head to tail fashion. This DNA can then be transformed into a microorganism.

In a second variation of this strategy, blunt cutting restriction enzymes can be substituted for BamH I and Bgl I. For example, Sma I and EcoR V can be substituted for BamH I and Bgl II, respectively. The digestion and fragment isolation are then carded out as above. An important feature of this strategy, common to both the blunt and complementary/nonisoschizomefic variations, is that the physiologic phasing of the arrays can be precisely maintained, if desired. Examples of additional blunt cutters that can be used include Ssp I, Stu I, Sca I, Pml I, Pvu II, Ecl136 II, Nae I, Ehe I, Hinc II, Hpa I, SnaB I, Nru I, Fsp I, Dra I, Msc I, Bst107 I, Alu I, Asp 700/Xmn I, Avi II, BbrP I, Bstl107 I, Eco47 III, Dpn I, Hae III, HindII, Nam I, MluM I, Mvn I, Rsa I, Swa I, Bsh1236 I, Eco72 I, Pal I, and SrfI.

Stability of the cloned plasmids containing large tandem arrays of synthetic alpha satellite DNA can be determined using simple growth and dilution experiments as described in Example 2. For example, stability can be determined by passage for 50 generations and subsequent analysis of plasmid DNA for structural integrity. Plasmid structure can be analyzed by restriction analysis, and agarose gel electrophoresis. Little or no recombination was observed for these clones, indicating that the directional cloning scheme can be employed to construct and propagate synthetic alpha satellite arrays in the context of a mini-F cloning vector (such as the pBAC108L vector) and a suitable *E. coli* host.

The method of the invention can be used to construct any desired repeating DNA unit. For example, alpha satellite DNA from any eukaryotic chromosome, especially human DNA, can be cloned. Other examples of large tandem arrays of highly repetitive DNA include the immunoglobulin, DNA loci, regions of heterochromatic repeats and telomeres.

The directional cloning method of the invention does not require the presence of polymorphic restriction sites, as required when cloning endogenous (nonmodified) arrays. Even when present, these sites do not permit control of the exact size of the array. Furthermore, by using a single higher order repeat as used in the method of the invention, (see FIG. 1), and sequentially doubling its size, the exact sequence of the entire array is known, since the sequence of the original higher order repeat is known.

When cloning endogenous arrays, such as, for example, endogenous alpha satellite arrays, one cannot be confident of the precise composition of a given array. In particular, interruptions in the arrays by non-repetitive DNA may have significant effects on stability in *E. coil*. In addition, to be suitable as a vector for gene therapy, one must know the exact sequence of the vector being provided to the recipient of such therapy. The method of the invention obviates that concern and allows the artisan to bypass sequencing of native alpha satellite arrays, in favor of constructing a useful array, de novo, from known repeating sequences.

Structurally diverged higher order repeats generally exhibit increased structural stability in *E. coli* relative to more homogeneous arrays. Thus, by utilizing homogeneous synthetic arrays according to the method of the invention, an accurate determination of the minimal stability of the repeating DNA in the vector can be obtained.

Any desired bacterial host in which the vector is stably maintained may be used as the host. Especially *E. coli* is useful when utilizing BAC vectors and the BAC system.

Synthetic alpha satellite arrays can be utilized in the construction of synthetic human chromosomes in the following manner: (1) by transfection of episomes containing synthetic alpha satellite arrays into a human or other mammalian cell line; (2) by transfection of episomes containing synthetic alpha satellite arrays in conjunction with randomly cloned human DNA or specific DNA fragments, into a human or other mammalian cell line; (3) by co-transfection into a human or other mammalian cell line of synthetic alpha satellite arrays with unlinked specific chromosomal components, such as telomeric DNA, matrix attachment regions, and/or other chromosomal loci that enhance the mitotic stability of alpha satellite containing episomal DNA. Co-transfection of these components in unlinked form allows the transfected cell line to construct an infinite number of structural permutations, permitting the most stable forms to be retained, while the unstable forms are lost, over time. Stable conformations can subsequently be harvested utilizing standard methods and procedures. Those constructs that exhibit episomal stability in the absence of selective pressure can be isolated and subsequently utilized in the preparation of gene therapy vectors containing one or more therapeutically useful entities such as genes, ribozymes, or antisense transcripts.

Having now generally described the invention, the same will be more readily understood through reference to the following examples which are provided by way of illustration, and are not intended to be limiting of the present invention, unless specified.

EXAMPLES

Example 1

Construction of Chromosome 17 Alpha Satellite Vectors

In order to clone and propagate alpha satellite DNA in *E. coli* using BAC vectors, a series of tandem alpha satellite arrays of various sizes were constructed.

The structure of the higher order alpha satellite repeat from human chromosome 17 has been described previously (Waye and Willard, *Mol. Cell. Biol.* 6(9): 3156–65 (1986)). The predominant higher order repeat of human chromosome 17 is 2.7 kb in length, and consists of 16 alphoid monomers flanked by EcoR I sites. A discrete structural unit of alpha satellite DNA, the higher order repeat, derived from human chromosome 17 or the human Y chromosome was cloned into the plasmid cloning vector pACYC184 (New England Biolabs) by digesting human genomic DNA with the restriction enzyme EcoR I. The nucleotide sequence of the cloned higher order repeats was verified by DNA sequence analysis.

Polymerase chain reaction (PCR) was used to amplify a single 2.7 kb higher order repeat monomer unit such that complementary restriction sites (BamH I and Bgl II) were created at opposing ends of the higher order register. The precise length of the higher order repeat was maintained. The primer pair used to amplify this fragment was
VB100-5' . . . gggcgggagatctcagaaaattctttgggatgattgagttg (SEQ ID NO: 1) and
VB 101-5' . . . gggcgggatccettctgtcttcttttataggaagttattt (SEQ ID NO: 2).

The modified higher order repeat was cloned into the BAC vector pBAC108L (a gift from Bruce Birren, California Institute of Technology, Pasadena, Calif.) by digesting the amplified fragment with BamH I, gel purifying the insert DNA, and ligating into vector DNA which had been digested with BamH I and Hpa I and gel purified. The resulting plasmid was designated pBAC-17α1.

To construct a synthetic alimet of alpha satellite DNA, aliquots of pBAC-17α1 were digested separately with either: (1) BamH I+Sfi I, or (2) Bgl II+Sfi I. Following gel electrophoresis, the 2.7 kb alpha satellite band from the Bgl II/Sfi I digest was excised and ligated to the excised pBAC-17α BamH I/Sfi I fragment. Since Bgl II and BamH I generate compatible overhangs, and Sfi I generates an asymmetric overhang that can only tellgate in a particular orientation, the 2.7 kb fragment ligates to the vector DNA to create a tandem dimer arrayed in head to tail fashion. Ligation products were transformed into the bacterial strain DH10B by electroporation. Clones were analyzed by restriction analysis, and those that contained a tandemly arrayed modified dimer of the chromosome 17 alpha satellite were designated pBAC-17α2 (FIG. 1). This strategy was repeated to create extended alpha satellite arrays consisting of 4, 8, 16, 32, 48, or 64 higher order alpha satellite repeats. A similar strategy was utilized to construct synthetic arrays of higher order repeats from other human chromosomes, such as the Y chromosome.

The construction of BAC vector containing 174 kb of alpha satellite DNA represents the largest amount of this class of DNA to be cloned and propagated in *E. coli* to date. Previous experiments have successfully cloned approximately 40 kb in *E. coli* using cosmids (Willard et al., *Prog. Clin. Biol. Res.* 318: 9–18 (1989)). Others have used medium copy number plasmids to clone arrays ranging in size from the about 171 bp alphoid monomer to 40 kb (Waye and Willard, *Nucleic Acids Res.* 15(18): 7549–69 (1987)). In the studies reported in the art, a high frequency of recombination was observed in the plasmids that contained the largest alphoid arrays. In contrast, during the propagation of the pBAC-17α64, we observed little evidence of recombination products utilizing standard methods of plasmid purification. Since instability of alpha satellite DNA has been shown in the context of these cloning vectors, we analyzed our preparations of pBAC-17α64 for the presence of obviously rearranged arrays utilizing gel electrophoresis. By this assay, the presence of significant levels of rearranged plasmid was not detectable.

Example 2

Stability assay

Although no evidence for high levels of recombination and/or deletion in the synthetic alpha satellite arrays from Example 1 was observed, it was possible that recombination was occurring at relatively high levels, but the large number of different deletion products prevented any one product from being detectable. Therefore, the rate of recombination of these constructs utilizing a highly sensitive assay was determined. In addition, because larger arrays might be expected to be less stable than smaller ones, several different size constructs were examined. The stability of these constructs was examined below.

Stability assays were carded out using three different alpha satellite array sizes which have been cloned into pBAC108L, as described above. These constructs, called pBAC-17α32, pBAC-17α48, and pBAC-170α64, contain 87 kb, 130 kb, and 174 kb of alpha satellite DNA, respectively. Following transformation (electroporation) into the *E. coli* strain, DH10B (GIBCO BRL), single clones were picked and analyzed. Because it is possible that the transformation process itself may lead to DNA rearrangements, only clones containing predominantly full-length constructs, as judged by restriction digest and electrophoresis, were saved as glycerol stocks.

To begin the stability assay, cells from a glycerol stock of each construct were streaked onto LB plates containing 12.5 µg/ml chloramphenicol. Eight of the resulting colonies were picked and grown individually to saturation in 5 ml of LB containing 12.5 µg/ml chloramphenlcol (approximately 20 generations). The plasmid DNA from each clone was then purified, digested with BamH I, and separated by pulse field gel electrophoresis. Clones that contained any full length plasmid were said to have full length plasmid at the single cell stage. Clones which did not contain any detectable full-length plasmid were said to be the result of a recombination event prior to restreaking (i.e., a rearrangement that occurred during production of the glycerol stock) and were excluded. Of the clones that contained some full-length plasmid, 10 cultures were picked at random, diluted 1 to one million into fresh LB containing 12.5 µg/ml chloramphenicol, and grown to saturation (approximately 30 generations). From a single cell to this final saturated culture, approximately 50 generations of growth have occurred.

In order to determine the percent of plasmids that rearranged during these 50 generations, each saturated culture was streaked onto LB plates containing 12.5 µg/ml chloramphenicol. Individual colonies were then grown to saturation in 1.5 ml LB containing 12.5 µg/ml chioramphenicol. Following growth, the DNA was purified and analyzed by restriction digest (BamH I) and PFGE. Any clone that contained detectable full length plasmid was scored as unrearranged during the 50 generation experiment. Conversely, any clone which did not contain any detectable full-length plasmid was scored as rearranged during the 50 generation experiment. To calculate the average rearrangement frequency per generation for each construct, the fraction of rearranged clones was determined after 50 generations. One minus this value is equal to the fraction of unrearranged clones (after 50 generations). The fraction of clones that rearrange after one generation is 1 minus the 50th root of the fraction of unrealranged clones after fifty generations. This is summarized in the following equation:

$$X=1-(1-Y)^{1/50}$$

where X is the fraction of clones which rearrange per generation and Y is the fraction of rearranged clones after 50 generations of growth.

Using this strategy, the recombination frequency of three alpha satellite containing constructs was determined. After 50 generations of growth, 0% (n=9) of the pBAC-17α32 clones recombined to truncated forms. Recombinants were detected for the pBAC-17α48 and pBAC-17α64 at a level of 8.5% (n=59) and 25% (n=84), respectively. This corresponds to a per generation recombination frequency of 0.18% for pBAC-17α48 and 0.57% for pBAC-17α64. Thus, this recombination frequency is significantly lower than that reported for other cloning vectors containing far less alphold DNA (for example, 40 kb) and which are grown for less generations (for example, 30 generations).

The results show that alpha satellite arrays up to at least 174 kb in size can be stably propagated in *E. coli* using BAC vectors in the methods of the invention. The 174 kb and 130 kb arrays recombine at a frequency of 0.57% and 0.18% per generation, respectively. Thus, using pBAC-17α64 as an example, following 50 generations of growth from a single cell, approximately 1,000 liters of saturated bacterial culture can be produced from a single cell and at least 75% of the cells will contain full-length pBAC-17α64, on average. This degree of rearrangement falls within the expected acceptable range for the large scale production of alpha satellite containing human artificial chromosomes for use in gene therapy.

Figure 2:
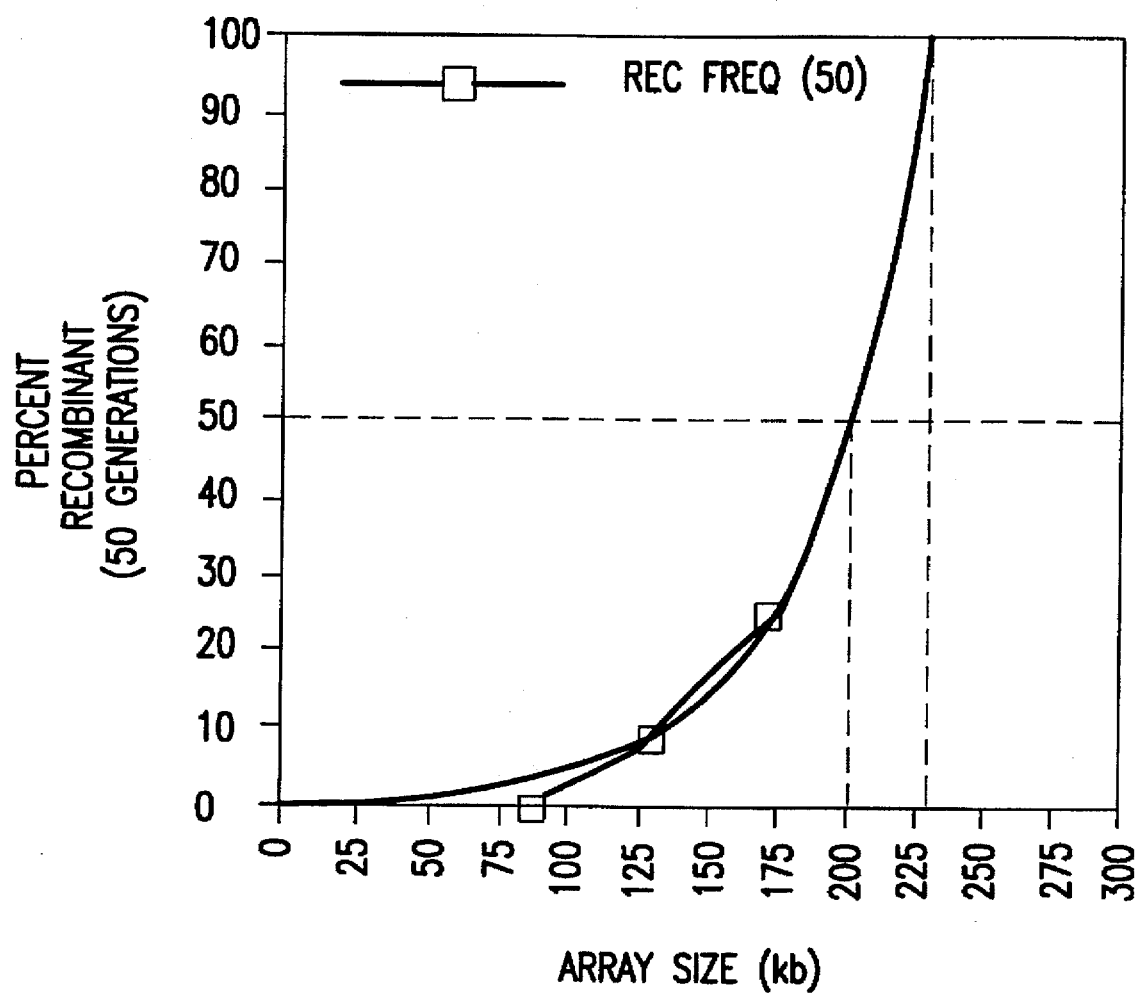
FIG. 2 is a graphical representation of the correlation of the percent recombinants (after 50 generations) and the array size (kb).

In addition to determining the frequency of alpha satellite DNA rearrangement in pBAC108L, a correlation between the size of a highly repetitive alpha satellite array and its stability in this vector was established. Based on the recombination frequencies determined above, the minimum upper size limit estimate of homogenous alpha satellite DNA in BAC vectors (assuming 50% full length clones after 50 generations to be acceptable) is conservatively between 200 and 215 kb (FIG. 2). This was determined by extrapolation using the computer program Cricket Graph. This is a minimum estimate of alphold capacity, as other lines are found that fit the data and produce larger estimates than those stated above. From this correlation, it is estimated that, when using 200–215 kb arrays, and propagation in bacterial strain DB10B, greater than 50% of the plasmid will be full length after 50 generations. It is likely that this upper size figure could be extended by utilizing the BAC vector in conjunction with specialized recombination defective bacterial strains. Furthermore, this estimate is based on maximally homogeneous arrays. The stability of diverged arrays including certain natural alpha satellite arrays should exceed this estimate.

The experiment described here represents the first stable cloning and propagation of an alpha satellite array larger than 50 kb in *E. coli*. Previously, alpha satellite DNA has been cloned in *E. coli* using cosmids (Haaf et al., *Cell* 70(4): 681–96 (1992). In addition to the relatively small size of these arrays (equal to or less than 40 kb), the integrity and stability of these arrays was not analyzed. Alpha satellite DNA has also been cloned using YAC's (Neil et al., *Nucleic Acids Res.* 18(6): 1421–8 (1990)). In these studies, the instability of the alpha satellite arrays was noted, and additional manipulations such as agarose gel purification was required to obtain preparations containing predominantly full-length arrays. In addition, there are certain disadvantages to using YAC's to propagate alpha satellite DNA. Perhaps the most important of these relates to the topology of YAC's. In general, YAC's are linear DNA molecules, and therefore, simple alkaline lysis purification methodology can not be used to puffy the alpha satellite construct away from contaminating yeast chromosomes. Instead, pulsed field gel electrophoresis (PFGE), a separation method which is not amenable to scale-up, must be used. Finally, the linear topology of YAC's renders them particularly susceptible to shearing during purification. Here, we have demonstrated that the alpha satellite containing BAC's can be harvested and purified away from *E. coli* chromosomal DNA without substantial shearing.

Previous studies suggest that alpha satellite DNA is an important component of the functional human centromere. Naturally occurring alpha satellite arrays range in size from 230 kb to several megabases in length (Oakey and Tyler, *Genomics* 7(3): 325–30 (1990)); (Wevrick and Willard, *Proc. Natl. Acad. Sci. USA* 86(23): 9394–8 (1989)). However, recent studies suggest that as little as 140 kb of alpha satellite DNA is sufficient to confer centromere function in human cells (Brown et al., *Human Molecular Genetics* 3(8): 1227–1237 (1994)). The alpha satellite array constructs described herein are the first that allow the large scale, stable production of alpha satellite arrays which are large enough to satisfy the alpha satellite requirements of a functional human centromere. These constructs can serve as the backbone of synthetic human chromosomes.

Example 3

Construction of Y Chromosome Alpha Satellite Vectors

Construction was as in example 1, except that DNA from the human male Y chromosome cell line GM07033. was used; DNA from any normal human male cell line would be equivalent. The predominant higher order alphoid repeat on the human Y chromosome is 5.7 kb in length, and is demarcated by flanking EcoR I sites. The 5.7 kb higher order repeat from the Y chromosome alphoid array was cloned into a standard *E. coli* cloning vector, pACYC184 (New England Biolabs). The ends of the higher order repeat were then modified using PCR to create a BamH I site at one end and a Bgl II site at the other, replacing the existing EcoR I site. The modified higher order repeats were cloned into the pBAC108L cloning vector as above.

Example 4

Construction of Hybrid Alpha Satellite Vectors

Construction was as in example 1, except that alphoid DNA from both human chromosome 17 and the human Y chromosome was used. Two types of arrays were constructed. One array was a simple alternating repeat wherein one higher order repeat unit of chromosome 17 alphoid DNA alternated with one higher order repeat unit from the Y chromosome alphoid DNA. The second type of array that was constructed alternated a dimetic unit of the chromosome 17 higher order repeat of alphoid DNa with one unit of the chromosome Y repeat of alphoid DNA. In each case, as with the above examples, the proper phasing of the higher order repeats derived from each chromosome was retained at the junction of the synthetic hybrid.

Although the foregoing refers to particular preferred embodiments, it will be understood that the present invention is not so limited. It will occur to those ordinarily skilled in the art that various modifications may be made to the disclosed embodiments and that such modifications are intended to be within the scope of the present invention.

What is claimed is:

1. A method of cloning repeating tandem arrays of DNA, said method comprising
   (a) preparing a first DNA unit such that the opposing ends of DNA unit contain complementary, but non-isoschizomeric restriction sites;
   (b) ligating said DNA unit into a vector;
   (c) linearizing said vector at one of said restriction sites;
   (d) ligating a second DNA unit, prepared as in step (a), in tandem with said first unit, so as to form a directional, repeating array;
   (e) transforming said array into a bacterial host cell;
   (f) selecting stable clones containing said array; and
   (g) repeating steps (c)–(f) until a desired array size is reached.

2. The method of claim 1, wherein said DNA is alpha satellite DNA.

3. The method of claim 2, wherein said array of said alpha satellite DNA is greater than 100 kb in length.

4. The method of claim 3, wherein said array of said alpha satellite DNA is greater than 140 kb in length.

5. The method of claim 2, wherein said alpha satellite DNA is human alpha satellite DNA.

6. A vector, said vector comprising a sequence consisting of a directional, repeating, DNA array, said array comprising repeating DNA units, wherein the opposing ends of each DNA unit contain complementary, but non-isoschizomeric restriction sites.

7. The vector of claim 6, wherein said DNA is alpha satellite DNA.

8. The vector of claim 7, wherein said array of said alpha satellite DNA is greater than 100 kb in length.

9. The vector of claim 8, wherein said array of said alpha satellite DNA is greater than 140 kb in length.

10. The vector of claim 7, wherein said alpha satellite DNA is human alpha satellite DNA.

11. A host cell, stably transformed with the vector of any one of claims 6–10.

12. The host cell of claim 11, wherein said host cell is a prokaryotic cell.

13. The host cell of claim 12, wherein said prokaryotic cell is *E. coli*.

14. The method of claim 1 wherein said DNA is repetitive DNA.

15. The method of claim 1 wherein said DNA is centromeric DNA.

16. The method of any of claims 1, 2, 14, or 15, wherein said vector is a BAC vector.

17. The vector of claim 6 wherein said DNA is repetitive DNA.

18. The vector of claim 6 wherein said DNA is centromeric DNA.

19. The vector of claim 6 wherein said array is at least around 20 kb.

20. The vector of any of claims 6, 7, and 17–19 wherein said vector is a BAC vector.

* * * * *